(12) United States Patent
Edidin et al.

(10) Patent No.: US 8,029,567 B2
(45) Date of Patent: Oct. 4, 2011

(54) PERCUTANEOUS SPINAL IMPLANTS AND METHODS

(75) Inventors: Avram Allan Edidin, Sunnyvale, CA (US); Andrew C. Kohm, Burlingame, CA (US); Hugues F. Malandain, Mountain View, CA (US)

(73) Assignee: Kyphon Sarl, Neuchatel (CH)

( * ) Notice: Subject to any disclaimer, the term of this patent is extended or adjusted under 35 U.S.C. 154(b) by 1372 days.

(21) Appl. No.: 11/356,295

(22) Filed: Feb. 17, 2006

(65) Prior Publication Data

US 2007/0049934 A1 Mar. 1, 2007

Related U.S. Application Data (63) Continuation-in-part of application No. 11/252,879, filed on Oct. 19, 2005, and a continuation-in-part of application No. 11/252,880, filed on Oct. 19, 2005, now abandoned, which is a continuation-in-part of application No. 11/059,526, filed on Feb. 17, 2005, now abandoned.

(60) Provisional application No. 60/695,836, filed on Jul. 1, 2005.

(51) Int. Cl.
*A61F 2/44* (2006.01)

(52) U.S. Cl. .................. 623/17.11; 606/86 A; 606/246; 606/279

(58) Field of Classification Search .......... 606/246–249, 606/90, 102, 279, 86 A; 623/17.11–17.16
See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,248,054 A | 7/1941 | Becker |
| 2,299,308 A | 10/1942 | Creighton |
| 2,472,103 A | 6/1949 | Giesen |
| 2,485,531 A | 10/1949 | Dzus et al. |
| 2,607,370 A | 8/1952 | Anderson |
| 2,677,369 A | 5/1954 | Knowles |

(Continued)

FOREIGN PATENT DOCUMENTS

DE 2821678 A1 11/1979

(Continued)

OTHER PUBLICATIONS

International Search Report for PCT/US06/05580 dated Nov. 9, 2006.

(Continued)

*Primary Examiner* — Eduardo C Robert
*Assistant Examiner* — Tara R Carter (57) ABSTRACT

Apparatuses and methods for performing minimally-invasive medical procedures are described. In one embodiment, for example, an apparatus includes an elongate member having a proximal portion configured to move repeatedly between a first configuration and a second configuration. At least a section of the proximal portion is collapsed in the first configuration and is expanded in the second configuration. The elongate member has a distal portion configured to move repeatedly between a first configuration and a second configuration. At least a section of the proximal portion is collapsed in the first configuration and is expanded in the second configuration. A non-expanding central portion is positioned between the proximal portion and the distal portion. The non-expanding central portion is configured to engage adjacent spinous processes.

6 Claims, 7 Drawing Sheets

U.S. PATENT DOCUMENTS

| | | |
|---|---|---|
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,486,505 A | 12/1969 | Morrison |
| 3,604,487 A | 9/1971 | Gilbert |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,509,517 A | 4/1985 | Zibelin |
| 4,519,100 A | 5/1985 | Wills et al. |
| 4,553,273 A | 11/1985 | Wu |
| 4,554,914 A | 11/1985 | Kapp et al. |
| 4,557,259 A | 12/1985 | Wu |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,862,891 A | 9/1989 | Smith |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,997,432 A | 3/1991 | Keller |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,097,820 A | 3/1992 | Shulman et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,484,440 A | 1/1996 | Allard |
| 5,489,307 A | 2/1996 | Kuslich et al. |
| 5,496,318 A | 3/1996 | Howland et al. |
| 5,518,498 A | 5/1996 | Lindenberg et al. |
| 5,536,268 A | 7/1996 | Griss |
| 5,545,170 A | 8/1996 | Hart |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,599,279 A | 2/1997 | Slotman et al. |
| 5,609,634 A | 3/1997 | Voydeville |
| 5,609,635 A | 3/1997 | Michelson |
| 5,609,636 A | 3/1997 | Kohrs et al. |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,662,657 A | 9/1997 | Carn |
| 5,665,096 A | 9/1997 | Yoon |
| 5,665,122 A | 9/1997 | Kambin |
| 5,667,513 A | 9/1997 | Torrie et al. |
| 5,674,295 A | 10/1997 | Ray et al. |
| 5,676,702 A | 10/1997 | Ratron |
| 5,683,464 A | 11/1997 | Wagner et al. |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,772,661 A | 6/1998 | Michelson |
| 5,792,085 A | 8/1998 | Walters |
| 5,797,909 A | 8/1998 | Michelson |
| 5,800,547 A | 9/1998 | Schafer et al. |
| 5,800,549 A | 9/1998 | Bao et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,888,224 A | 3/1999 | Beckers et al. |
| 5,893,890 A | 4/1999 | Pisharodi |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,042,582 A | 3/2000 | Ray |
| 6,048,342 A | 4/2000 | Zucherman et al. |
| 6,059,829 A | 5/2000 | Schlapfer et al. |
| 6,068,630 A | 5/2000 | Zucherman et al. |
| 6,074,390 A | 6/2000 | Zucherman et al. |
| 6,083,225 A | 7/2000 | Winslow et al. |
| 6,086,595 A | 7/2000 | Yonemura et al. |
| 6,113,602 A | 9/2000 | Sand |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,139,549 A | 10/2000 | Keller |
| 6,159,212 A | 12/2000 | Schoedinger, III et al. |
| 6,171,339 B1 | 1/2001 | Houfburg et al. |
| 6,174,311 B1 | 1/2001 | Branch et al. |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,224,607 B1 | 5/2001 | Michelson |
| 6,224,631 B1 | 5/2001 | Kohrs |

| Patent | Date | Name |
|---|---|---|
| 6,241,729 B1 | 6/2001 | Estes et al. |
| 6,245,107 B1 | 6/2001 | Ferree |
| 6,261,296 B1 | 7/2001 | Aebi et al. |
| 6,261,586 B1 | 7/2001 | McKay |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,565,570 B2 | 5/2003 | Sterett et al. |
| 6,582,433 B2 | 6/2003 | Yun |
| 6,582,467 B1 | 6/2003 | Teitelbaum et al. |
| 6,592,585 B2 | 7/2003 | Lee et al. |
| 6,602,260 B2 | 8/2003 | Harari et al. |
| 6,610,065 B1 | 8/2003 | Branch et al. |
| 6,626,944 B1 | 9/2003 | Taylor |
| 6,645,207 B2 | 11/2003 | Dixon et al. |
| 6,652,533 B2 | 11/2003 | O'Neil |
| 6,669,729 B2 | 12/2003 | Chin |
| 6,676,665 B2 | 1/2004 | Foley et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,712,819 B2 | 3/2004 | Zucherman et al. |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,743,257 B2 | 6/2004 | Castro |
| 6,752,832 B2 | 6/2004 | Neumann |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,857,343 B1 | 2/2005 | Easterbrooks et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,189,234 B2 | 3/2007 | Zucherman et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,252,673 B2 | 8/2007 | Lim |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,524,324 B2 | 4/2009 | Winslow et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,901,430 B2 | 3/2011 | Matsuura et al. |
| 2001/0012938 A1 | 8/2001 | Zucherman et al. |
| 2001/0016743 A1 | 8/2001 | Zucherman et al. |
| 2002/0082600 A1 | 6/2002 | Shaolian et al. |
| 2002/0143331 A1 | 10/2002 | Zucherman et al. |
| 2002/0161368 A1 | 10/2002 | Foley et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0120328 A1 | 6/2003 | Jenkins et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0059318 A1 | 3/2004 | Zhang et al. |
| 2004/0087947 A1 | 5/2004 | Lim et al. |
| 2004/0097931 A1 | 5/2004 | Mitchell |
| 2004/0106927 A1 | 6/2004 | Ruffner et al. |
| 2004/0106995 A1 | 6/2004 | Le Couedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0138662 A1 | 7/2004 | Landry et al. |
| 2004/0167625 A1 | 8/2004 | Beyar et al. |
| 2004/0199255 A1 | 10/2004 | Mathieu et al. |
| 2004/0249388 A1 | 12/2004 | Michelson |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0085814 A1 | 4/2005 | Sherman et al. |
| 2005/0090824 A1 | 4/2005 | Shluzas et al. |
| 2005/0113832 A1 | 5/2005 | Molz, IV et al. |
| 2005/0113842 A1 | 5/2005 | Bertagnoli et al. |
| 2005/0119665 A1 | 6/2005 | Keller |
| 2005/0143827 A1 | 6/2005 | Globerman et al. |
| 2005/0149035 A1 | 7/2005 | Pimenta et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0216002 A1 | 9/2005 | Simonson |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0277934 A1 | 12/2005 | Vardiman |
| 2005/0278036 A1 * | 12/2005 | Leonard et al. ............ 623/23.47 |
| 2005/0288672 A1 | 12/2005 | Feree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0036254 A1 | 2/2006 | Lim |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 * | 4/2006 | Kim ........................ 623/17.11 |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |

| | | |
|---|---|---|
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235426 A1 | 10/2006 | Lim et al. |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0100340 A1 | 5/2007 | Lange et al. |
| 2007/0112354 A1 | 5/2007 | Iwasaki et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0191833 A1 | 8/2008 | Heathcote |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| DE | 3922044 A1 | 2/1991 |
| DE | 4012622 C1 | 7/1991 |
| DE | 4217660 A1 | 12/1993 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 81 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003-079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | 2004/084743 A1 | 10/2004 |
| WO | 2004/084768 A2 | 10/2004 |
| WO | 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | 2006/064356 A1 | 6/2006 |
| WO | WO 2007/034516 A1 | 3/2007 |
| WO | 2007/052975 A1 | 5/2007 |

| | | |
|---|---|---|
| WO | 2009/083276 A1 | 7/2009 |
| WO | 2009/083583 A1 | 7/2009 |
| WO | 2009/098536 A1 | 8/2009 |

OTHER PUBLICATIONS

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. 5186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societá di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "DIAM Device For Low Back Pain In Degenerative Disc Disease 24 Months Follow-up," Advances in Minimally Invasive Surgery And Therapy For Spine And Nerves, Alexandre et al., eds., 2011, pp. 177-182, Spinger-Verlat/Wien.

Phillips et al., "Biomechanics of Posterior Dynamic Stabilizing Device (DIAM) After Facetectomy and Discectomy," The Spine Journal, 2006, vol. 6, pp. 714-722.

Taylor et al., "Device for Intervertebral Assisted Motion: Technique and Initial Results," Neurosurg, Focus, Jan. 2007, vol. 22, No. 1, pp. 1-6.

Wilke et al., "Biomechanical Effect of Different Lumbar Interspinous Implants on Flexibility and Intradiscal Pressure," Eur, Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

PERCUTANEOUS SPINAL IMPLANTS AND METHODS

CROSS-REFERENCE TO RELATED APPLICATIONS

This application is a continuation-in-part of U.S. patent application Ser. No. 11/252,879, entitled "Percutaneous Spinal Implants and Methods," filed Oct. 19, 2005; and U.S. patent application Ser. No. 11/252,880, entitled "Percutaneous Spinal Implants and Methods," filed Oct. 19, 2005, now abandoned each of which is a continuation-in-part of U.S. patent application Ser. No. 11/059,526, entitled "Apparatus and Method for Treatment of Spinal Conditions," filed Feb. 17, 2005 now abandoned and claims the benefit of U.S. Provisional Application Ser. No. 60/695,836 entitled "Percutaneous Spinal Implants and Methods," filed Jul. 1, 2005, each of which is incorporated herein by reference in its entirety.

This application is related to U.S. patent application each entitled "Percutaneous Spinal Implants and Methods," and filed on even date herewith, each of which is incorporated herein by reference in its entirety.

BACKGROUND

The invention relates generally to percutaneous spinal implants, and more particularly, to percutaneous spinal implants for implantation, for example, between adjacent spinous processes and optional subsequent removal therefrom.

A back condition that impacts many individuals is spinal stenosis. Spinal stenosis is a progressive narrowing of the spinal canal that causes compression of the spinal cord. Each vertebra in the spinal column has an opening that extends through it. The openings are aligned vertically to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. In some cases, bending forward may create more vertebral space, which may temporarily relieve nerve compression. Because spinal stenosis is a progressive disease, the source of pressure is often corrected surgically (e.g., decompressive laminectomy) when the patient has increasing pain over time. Known surgical procedures can remove bone and other tissues that have impinged upon the spinal canal or put pressure on the spinal cord. For example, two adjacent vertebrae can also be fused during the surgical procedure to prevent an area of instability, improper alignment or slippage, such as that caused by spondylolisthesis. Alternatively, decompression can relieve pressure on the spinal cord or spinal nerve by widening the spinal canal to define more space. This procedure requires that the patient be given a general anesthesia because an incision is made in the patient to access the spine to remove the areas that are contributing to the pressure. This procedure, however, may result in blood loss and an increased chance of significant complications, and usually results in an extended hospital stay.

Minimally invasive procedures have been developed to provide access to the space between adjacent spinous processes such that major surgery is not required.

Known medical devices have been developed to be permanently implanted between spinous processes. Such devices, however, can be subject to wear or can cause collateral conditions that would necessitate the removal of the medical device. The removal of the medical device can be difficult to accomplish percutaneously.

Thus, a need exists for improvements in devices and methods for the treatment of spinal conditions such as spinal stenosis.

SUMMARY OF THE INVENTION

Apparatuses and methods for performing minimally-invasive medical procedures are described herein. In one embodiment, for example, an apparatus includes an elongate member having a proximal portion configured to move repeatedly between a first configuration and a second configuration. At least a section of the proximal portion is collapsed in the first configuration and is expanded in the second configuration. The elongate member has a distal portion configured to move repeatedly between a first configuration and a second configuration. At least a section of the proximal portion is collapsed in the first configuration and is expanded in the second configuration. A non-expanding central portion is positioned between the proximal portion and the distal portion. The non-expanding central portion is configured to engage adjacent spinous processes.

DETAILED DESCRIPTION

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

An apparatus includes an elongate member having a proximal portion configured to be repeatedly moved between a first configuration and a second configuration under, for example, an axial load or a radial load. The elongate member has a distal portion configured to be moved from a first configuration to a second configuration under, for example, an axial load or a radial load. A non-expanding central portion is positioned between the proximal portion and the distal portion. The non-expanding central portion is configured to engage adjacent spinous processes upon spinal extension.

In some embodiments, the elongate member can have multiple portions that each move from a first configuration to a second configuration, either simultaneously or serially. Additionally, the device, or portions thereof, can be configured into many intermediate positions during the movement between the first configuration and the second configuration. For ease of reference, the entire device is referred to as being in either a first configuration or a second configuration although it should be understood that the device and/or portions thereof have a range of motion that includes many configuration including the first configuration and the second configuration.

Figure 1:
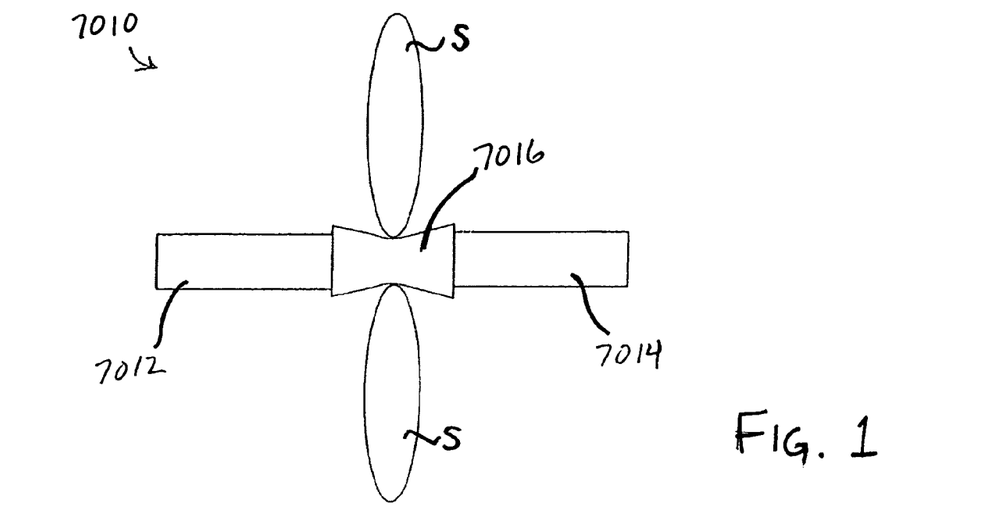
FIG. 1 is a schematic illustration of a posterior view of a medical device according to an embodiment of the invention in a first configuration adjacent two adjacent spinous processes.

FIG. 1 is a schematic illustration of a medical device according to an embodiment of the invention adjacent two adjacent spinous processes. The medical device 7010 includes a proximal portion 7012, a distal portion 7014 and a central portion 7016. The medical device 7010 has a first configuration in which it can be inserted between adjacent spinous processes S or removed from between adjacent spinous processes S. The central portion 7016 is configured to contact the spinous processes S to prevent over-extension/compression of the spinous processes S. In some embodiments, the central portion 7016 does not substantially distract the adjacent spinous processes S. In other embodiments, the central portion 7016 does not distract the adjacent spinous processes S. The medical device 7010 is inserted into a patient's back and moved in between adjacent spinous processes from the side of the spinous processes (i.e., a posterior-lateral approach). The use of a curved insertion shaft assists in the use of a lateral approach to the spinous processes S.

In the first configuration, the proximal portion 7012, the distal portion 7014 and the central portion 7016 share a common longitudinal axis. In other embodiments, these portions do not share a common longitudinal axis. In some embodiments, the proximal portion 7012, the distal portion 7014 and the central portion 7016 define a tube having a constant inner diameter. In other embodiments, the proximal portion 7012, the distal portion 7014 and the central portion 7016 define a tube having a constant outer diameter and/or inner diameter. In yet other embodiments, the proximal portion 7012, the distal portion 7014 and/or the central portion 7016 have different inner diameters and/or outer diameters.

Figure 2:
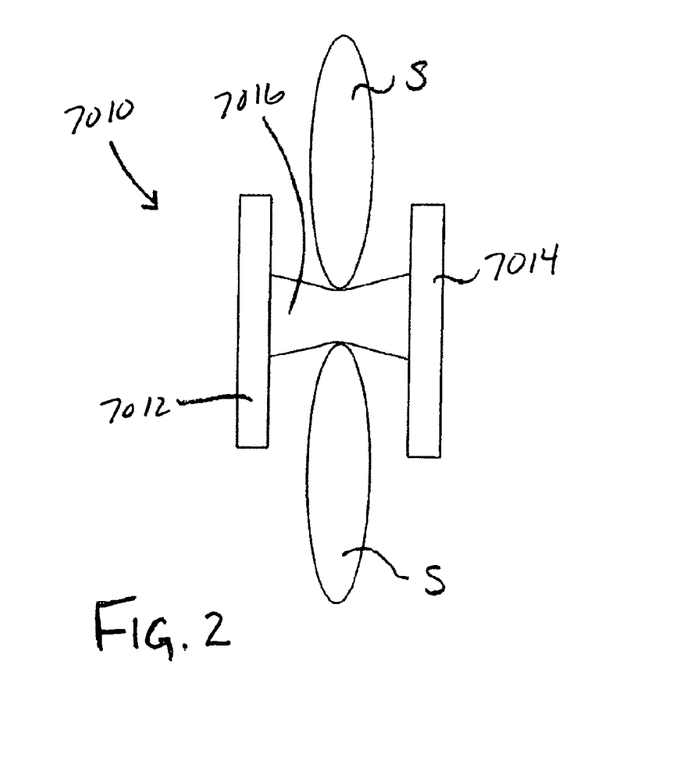
FIG. 2 is a schematic illustration of a posterior view of a medical device according to an embodiment of the invention in a second configuration adjacent two adjacent spinous processes.

The medical device 7010 can be moved from the first configuration to a second configuration as illustrated in FIG. 2. In the second configuration, the proximal portion 7012 and the distal portion 7014 are positioned to limit lateral movement of the device 7010 with respect to the spinous processes S. The proximal portion 7012 and the distal portion 7014 are configured to engage the spinous process (i.e., either directly or through surrounding tissue) in the second configuration. For purposes of clarity, the tissue surrounding the spinous processes S is not illustrated. Note the medical device and/or its portions can engage the spinous processes S during all or just a portion of the range of motion of the spinous processes S associated with the patient's movements.

In some embodiments, the proximal portion 7012, the distal portion 7014 and the central portion 7016 are monolithically formed. In other embodiments, one or more of the proximal portion 7012, the distal portion 7014 and the central portion 7016 are separate components that can be coupled together to form the medical device 7010. For example, the proximal portion 7012 and distal portion 7014 can be monolithically formed and the central portion 7016 can be a separate component that is coupled thereto. The proximal portion 7012, the distal portion 7014 and the central portion 7016 can be the same or different materials. These various portions can be coupled, for example, by a friction fit, welding, adhesive, etc.

In use, the spinous processes S can be distracted prior to inserting the medical device 7010. Distraction of spinous processes is disclosed, for example, in U.S. application Ser. No. 11/059,526, incorporated herein by reference in its entirety. When the spinous processes are distracted, a trocar can be used to define an access passage for the medical device 7010. In some embodiments, the trocar can be used to define the passage as well as distract the spinous processes S. Once an access passage is defined, the medical device 7010 is inserted percutaneously and advanced between the spinous processes, distal end 7014 first, until the central portion 7016 is located between the spinous processes S. Once the medical device 7010 is in place between the spinous processes, the proximal portion 7012 and the distal portion 7014 are moved to the second configuration, either serially or simultaneously.

In some embodiments, the medical device 7010 is inserted percutaneously (i.e., through an opening in the skin) and in a minimally-invasive manner. For example, as discussed in detail herein, when inserted, the sizes of portions of the implant are smaller than the size of the opening. The sizes of portions of the implant are expanded after the implant is inserted between the spinous processes. Once expanded, the sizes of the expanded portions of the implant are greater than the size of the opening. When collapsed, the sizes of portions of the spinal implant are again smaller than the size of the opening. For example, the size of the opening/incision in the skin can be between 3 millimeters in length and 25 millimeters in length across the opening. In some embodiments, the size of the implant in the expanded configuration is between 3 and 25 millimeters across the opening.

In some embodiments, the proximal portion 7012 and the distal portion 7014 can be moved back to their original configuration or substantially close to their original configuration and either repositioned between the adjacent spinous processes or removed from the body in which they were inserted.

Figure 3:
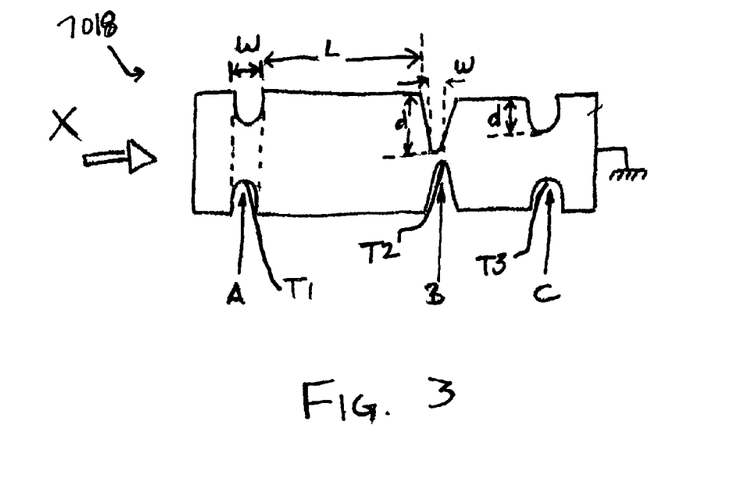
FIG. 3 is a schematic illustration of a deforming element according to an embodiment of the invention in a first configuration.

FIG. 3 is a schematic illustration of a deformable element 7018 that is representative of the characteristics of, for example, the distal portion 7014 of the medical device 7010 in a first configuration. The deformable member 7018 includes cutouts A, B, C along its length to define weak points that allow the deformable member 7018 to deform in a predetermined manner. Depending upon the depth d of the cutouts A, B, C and the width w of the throats T1, T2, T3, the manner in which the deformable member 7018 deforms under an applied load can be controlled and varied. Additionally, depending upon the length L between the cutouts A, B, C (i.e., the length of the material between the cutouts), the manner in which the deformable member 7018 deforms can be controlled and varied.

Figure 4:
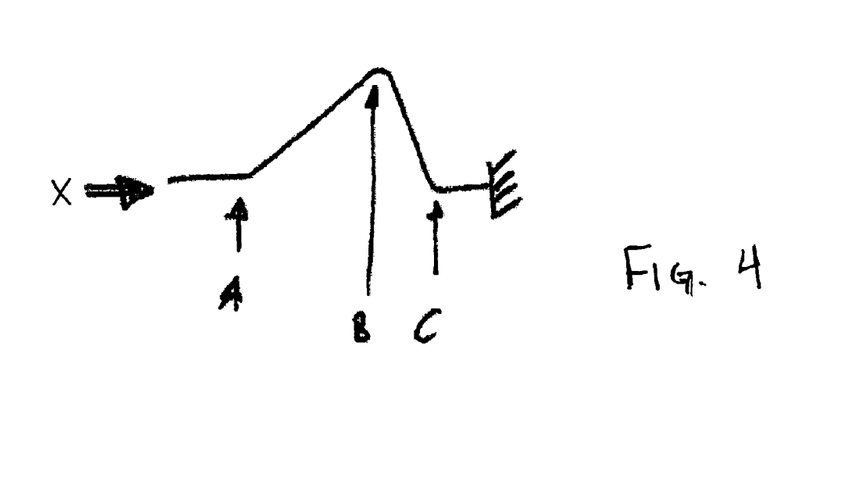
FIG. 4 is a schematic illustration of a side view of the expanding element illustrated in FIG. 3.

FIG. 4 is a schematic illustration of the expansion properties of the deformable member 7018 illustrated in FIG. 3. When a load is applied, for example, in the direction indicated by arrow X, the deformable member 7018 deforms in a predetermined manner based on the characteristics of the deformable member 7018 as described above. As illustrated in FIG. 4, the deformable member 7018 deforms most at cutouts B and C due to the configuration of the cutout C and the short distance between cutouts B and C. In some embodiments, the length of the deformable member 7018 between cutouts B and C is sized to fit one side of adjacent spinous processes.

The deformable member 7018 is stiffer at cutout A due to the shallow depth of cutout A. As indicated in FIG. 4, a smooth transition is defined by the deformable member 7018 between cutouts A and B. Such a smooth transition causes less stress on the tissue surrounding a side of adjacent spinous processes than a more drastic transition (i.e., a steeper angled wall) such as between cutouts B and C. The dimensions and configuration of the deformable member 7018 can also determine the timing of the deformation at the various cutouts. The weaker (i.e., deeper and wider) cutouts deform before the stronger (i.e., shallower and narrower) cutouts. It is intended that the deformable member 7018 undergoes plastic deformation when being deformed from the first configuration (e.g., FIG. 3) to the expanded second configuration.

Figure 5:
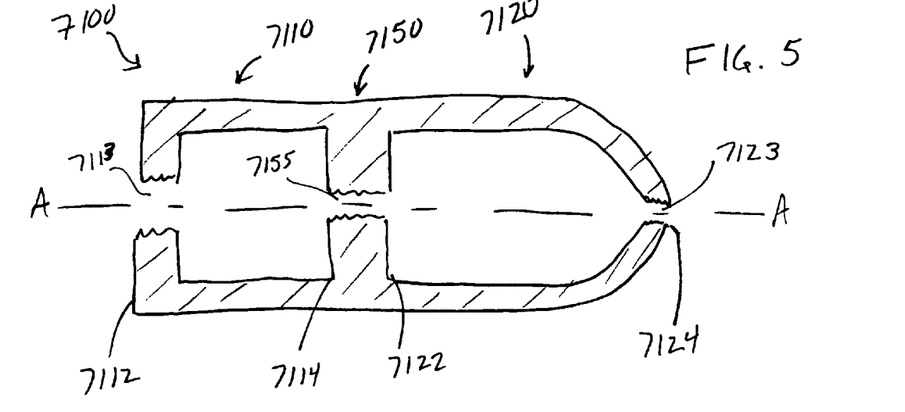
FIG. 5 is a side cross-sectional view of a medical device according to an embodiment of the invention in a first configuration.
Figure 6:
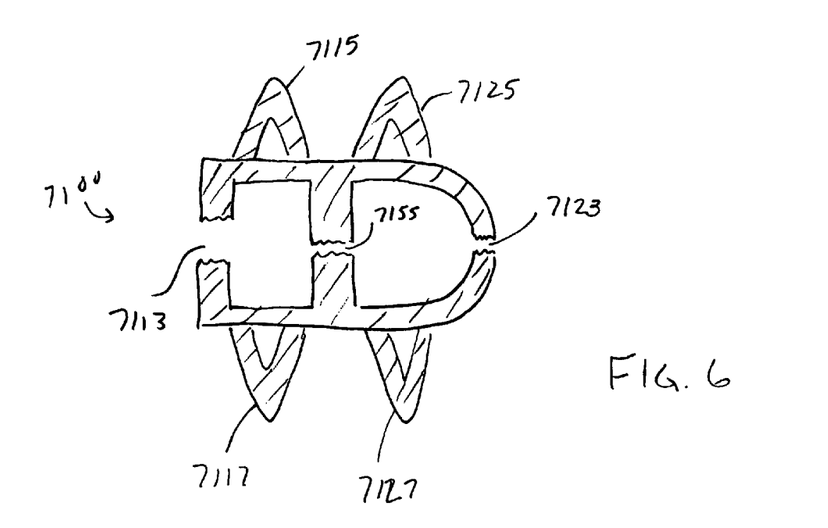
FIG. 6 is a side cross-sectional view of the medical device illustrated in FIG. 5 in a second configuration.

FIGS. 5 and 6 illustrate a spinal implant 7100 in a first configuration and second configuration, respectively. As shown in FIG. 5, the spinal implant 7100 is collapsed in a first configuration and can be inserted between adjacent spinous processes. The spinal implant 7100 has a first deformable portion 7110, a second deformable portion 7120 and a central, non-deformable portion 7150. The first deformable portion 7110 has a first end 7112 and a second end 7114. The second deformable portion 7120 has a first end 7122 and a second end 7124. The central portion 7150 is coupled between second end 7114 and first end 7122. In some embodiments, the spinal implant 7100 is monolithically formed.

The first deformable portion 7110, the second deformable portion 7120 and the central portion 7150 have a common longitudinal axis A along the length of spinal implant 7100. The central portion 7150 can have the same inner diameter as first deformable portion 7110 and the second deformable portion 7120. In some embodiments, the outer diameter of the central portion 7150 is smaller than the outer diameter of the first deformable portion 7110 and the second deformable portion 7120.

In use, spinal implant 7100 is inserted percutaneously between adjacent spinous processes. The first deformable portion 7110 is inserted first and is moved past the spinous processes until the central portion 7150 is positioned between the spinous processes. The outer diameter of the central portion 7150 can be slightly smaller than the space between the spinous processes to account for surrounding ligaments and tissue. In some embodiments, the central portion 7150 directly contacts the spinous processes between which it is positioned. In some embodiments, the central portion of spinal implant 7100 is a fixed size and is not compressible or expandable. Note the spinal implant 7100 and/or the first deformable portion 7110, second deformable portion 7120, and central portion 7150 can engage the spinous processes during all or just a portion of the range of motion of the spinous processes associated with the patient's movement.

The first deformable portion 7110 includes, for example, expanding members 7115, and 7117. Between the expanding members 7115, 7117, openings (not illustrated) are defined. As discussed above, the size and shape of the openings influence the manner in which the expanding members 7115, 7117 deform when an axial load is applied. The second deformable portion 7120 includes expanding members 7125 and 7127. Between the expanding members 7125, 7127, openings (not illustrated) are defined. As discussed above, the sizes and shapes of the openings influence the manner in which the expanding members 7125, 7127 deform when an axial load is applied.

When an axial load is applied to the spinal implant 7100, the spinal implant 7100 expands to a second configuration as illustrated in FIG. 6. In the second configuration, first end 7112 and second end 7114 of the first deformable portion 7110 move towards each other and expanding members 7115, 7117 project substantially laterally away from the longitudinal axis A. Likewise, first end 7122 and second end 7124 of the second deformable portion 7120 move towards one another and expanding members 7125, 7127 project laterally away from the longitudinal axis A. The expanding members 7115, 7117, 7125, 7127 in the second configuration form projections that extend to positions adjacent to the spinous processes between which the spinal implant 7100 is inserted. In the second configuration, the expanding members 7115, 7117, 7125, 7127 inhibit lateral movement of the spinal implant 7100, while the central portion 7150 prevents the adjacent spinous processes from moving together any closer than the distance defined by the diameter of the central portion 7150 during spinal extension.

The first end 7112 of the first deformable portion 7110 defines a threaded opening 7113. The central portion 7150 defines a second threaded opening 7155. The second end 7124 of the second deformable portion 7120 defines a third threaded opening 7123. The threaded openings 7113, 7155, 7123 receive portions of an actuator 7200 (see FIG. 7) to move the first deformable portion 7100 and the second deformable portion 7120 between their respective first configurations and second configurations as described in greater detail herein. In some embodiments, the first threaded opening 7113 has a greater diameter than the second threaded opening 7155 and the third threaded opening 7123 (see FIGS. 5-8). In some embodiments the second threaded opening 7155 and the third threaded opening 7123 have the same diameter (see FIGS. 5-8). In other embodiments, the first threaded opening 7113' and the second threaded opening 7155' have the same diameter (see FIGS. 9-12) and the third threaded opening 7123' has a smaller diameter than the first threaded opening and the second threaded opening. The threaded openings 7113, 7155, 7123, 7113', 7155', 7123' are coaxially aligned. In other embodiments, the threaded openings can be any combination of different or the same sizes.

Figure 7:
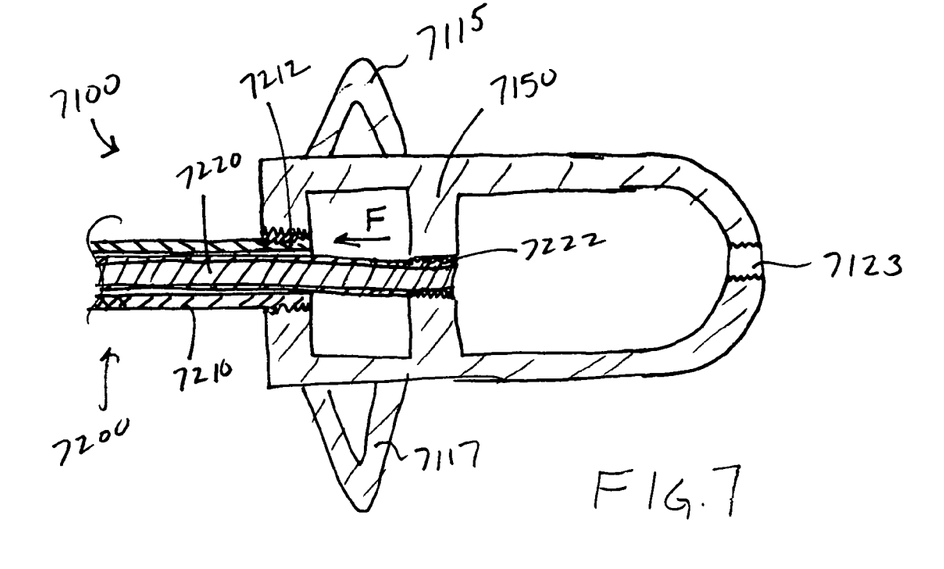
FIG. 7 is a cross-sectional side view of a medical device and an actuator according to an embodiment of the invention with a portion of the medical device deployed in a second configuration.

The spinal implant 7100 is deformed by a compressive force imparted substantially along the longitudinal axis A of the spinal implant 7100. As illustrated in FIG. 7, the compressive force is imparted to the first deformable portion 7110 by actuator 7200. The actuator includes a first portion 7210 and a second portion 7220 movably received within first portion 7210. In some embodiments, the second portion 7220 is slidably received within the first portion 7210. In other embodiments, the first portion 7210 and the second portion 7220 are threadedly coupled. Each of the first portion 7210 and the second portion 7220 is provided with external threads 7212 and 7222, respectively, to engage the threaded openings 7113, 7155, 7123, 7113', 7155', 7123'.

As illustrated in FIG. 7, the compressive force is imparted to the first deformable portion 7110, for example, by attaching the threaded portion 7212 to the first threaded opening 7113, attaching the threaded portion 7222 to the second threaded opening 7155 of the central portion 7150, and drawing the second portion 7220 along the longitudinal axis A while imparting an opposing force against the first end 7112 of the first deformable portion 7110. The opposing force results in a compressive force causing the spinal implant 7100 to expand as discussed above.

Figure 8:
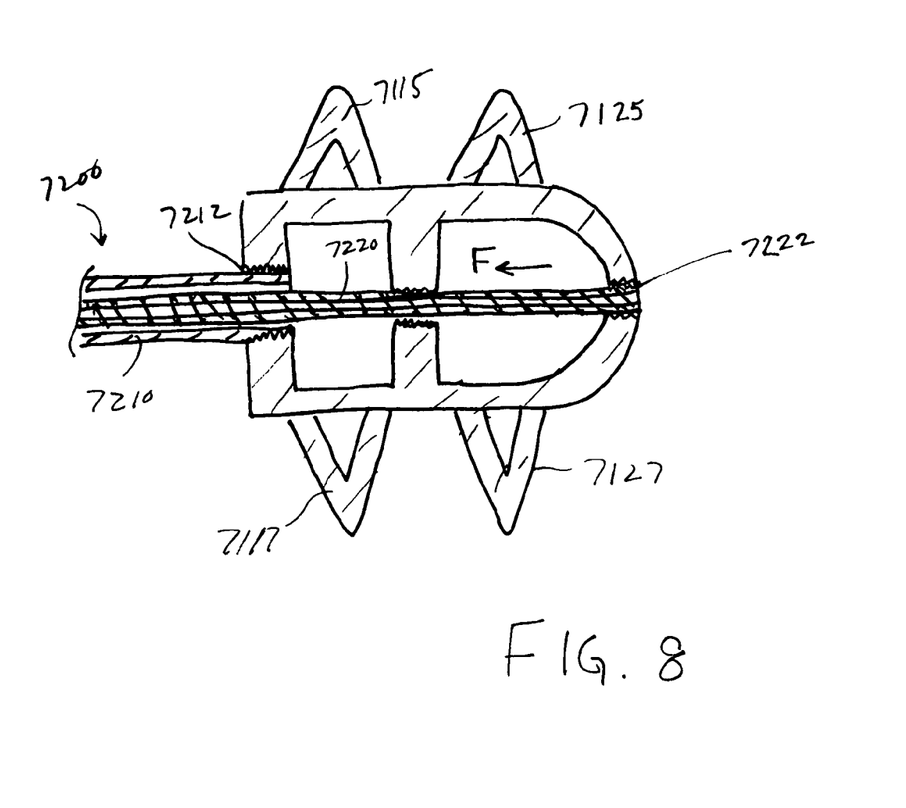
FIG. 8 is a side cross-sectional view of a medical device and an actuator according to an embodiment of the invention with the medical device fully deployed in the second configuration.
Figure 9:
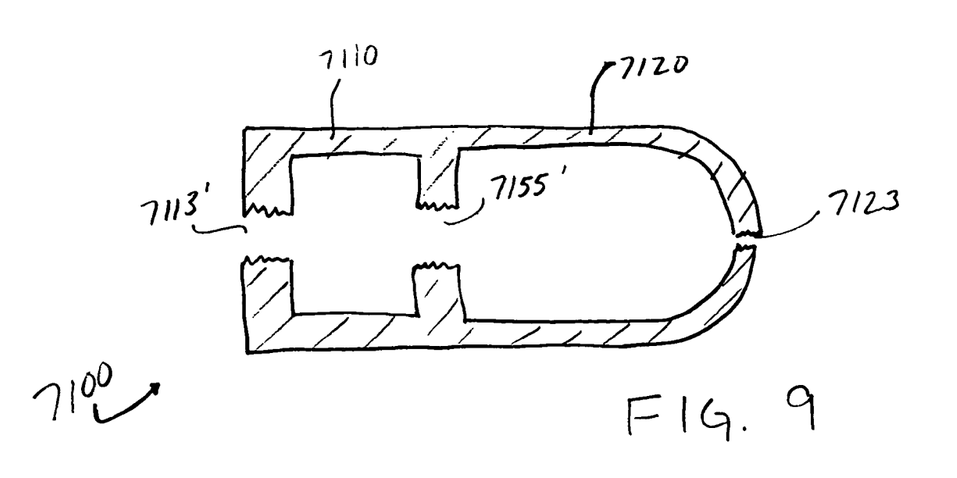
FIG. 9 is a side cross-sectional view of a medical device according to another embodiment of the invention in a first configuration.
Figure 10:
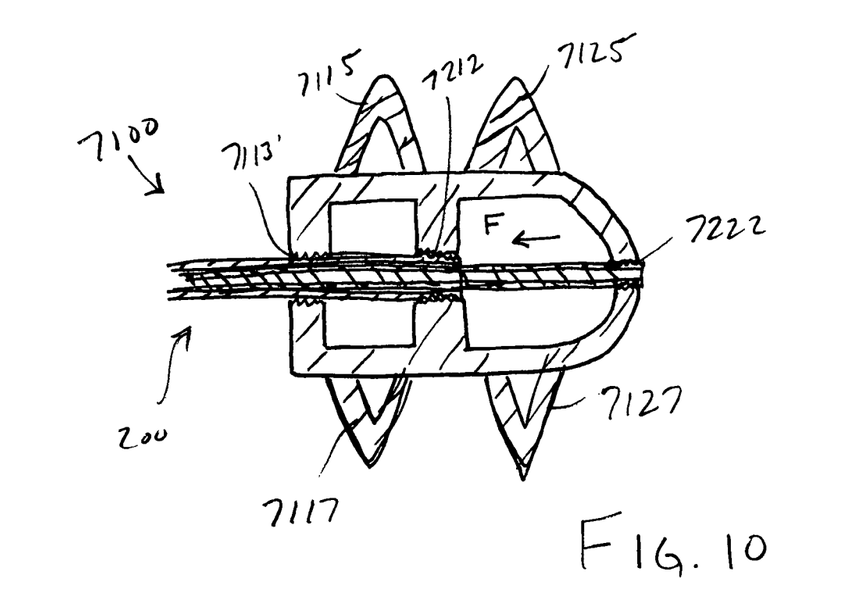
FIG. 10 is a side cross-sectional view of the medical device illustrated in FIG. 9 in a second configuration.

Once the first deformable portion 7110 is moved to its second configuration, the threaded portion 7222 is threaded through the second threaded opening 7155 and threadedly coupled to the third threaded opening 7123. A compressive force is imparted to the second deformable portion 7120 of the spinal implant 7100 by drawing the second portion 7220 of the actuator in the direction indicated by the arrow F while applying an opposing force using the first portion 7210 of the actuator against the spinal implant 7100. The opposing forces result in a compressive force causing the spinal implant to expand as illustrated in FIG. 8.

In some embodiments, the first deformable portion 7110 and the second deformable portion 7120 can be expanded simultaneously when the second portion 7220 of the actuator is coupled to the third threaded opening 7123 and the first portion 7210 is coupled to the first threaded opening 7113 and a compressive force is applied.

In embodiments in which the first threaded opening 7113' has the same diameter as the second threaded opening 7155' (best seen, for example, in FIGS. 9 and 10), the first threaded portion 7212 can be threadedly coupled to the second threaded opening 7155' and the second threaded portion 7222 can be threadedly coupled to the third threaded opening 7123'. A compressive force is then applied between the central portion 7150 and the second end 7124 of the second deformable portion 7120. Once the second deformable portion 7120 is in its second configuration, the first threaded portion 7212 can be threadedly coupled to the first threaded opening 7113' and the first deformable portion 7110 can be deformed into its second configuration.

Figure 11:
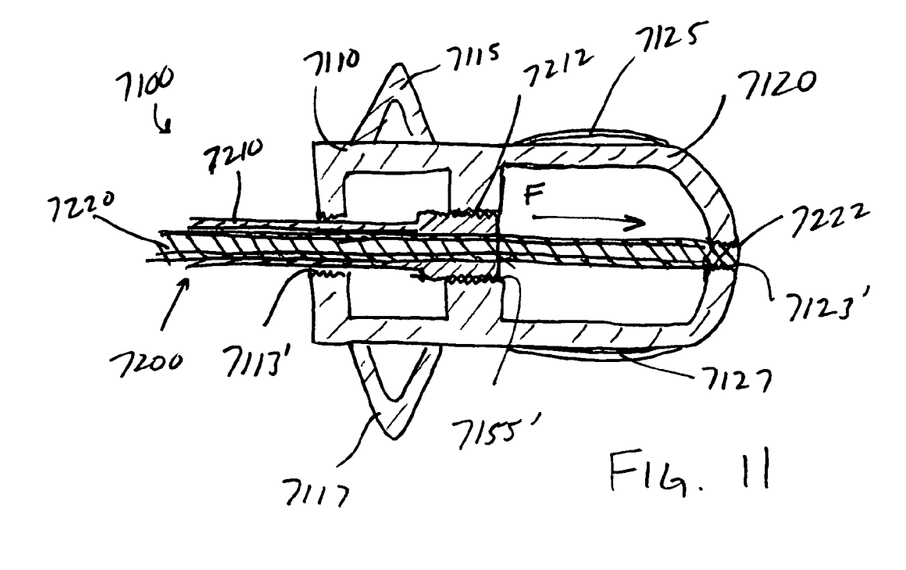
FIG. 11 is a side cross-sectional view of a medical device and an actuator according to an embodiment of the invention with a portion of the medical device moved back to its first configuration.
Figure 12:
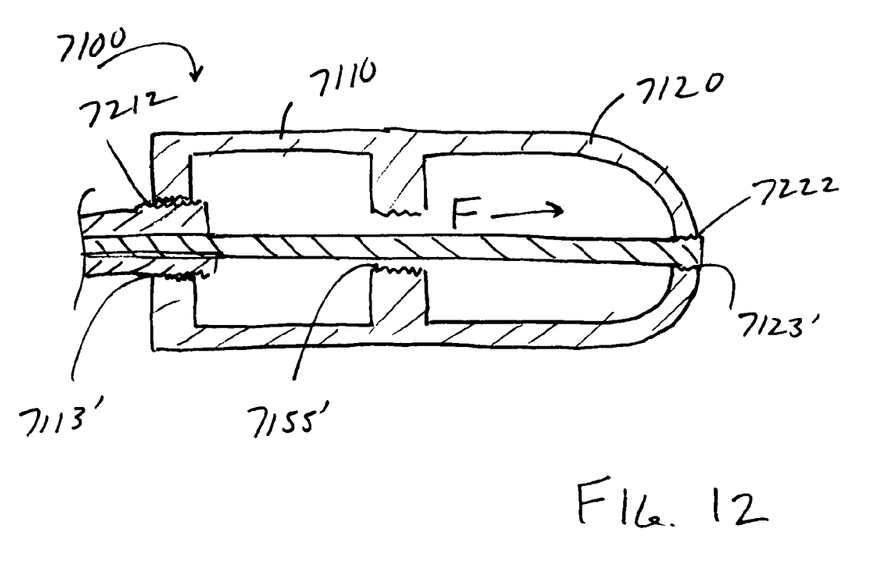
FIG. 12 is a side cross-sectional view of a medical device and an actuator according to an embodiment of the invention with the medical device moved back to its first configuration.

After each of the first deformable portion 7110 and the second deformable portion 7120 are moved to the second expanded configuration, they subsequently can each be moved back to the first collapsed configuration by applying a force in the opposite direction along longitudinal axis A as illustrated, for example, in FIGS. 11-12. In this example, as discussed above, the spinal implant 7100 illustrated in FIGS. 9-12 has a first threaded opening 7113' that has the same diameter as the second threaded opening 7155'.

With the first threaded portion 7212 coupled to the second threaded opening 7155' and the second threaded portion 7222 coupled to the third threaded opening 7123', the second portion 7220 of the actuator 7200 is moved in the direction indicated by arrow F to move the second deformable portion 7120 to its first collapsed configuration.

The first threaded portion 7212 is then coupled to the first threaded opening 7113' and the second portion 7220 of actuator 7200 is again moved in the direction of arrow F to move the first deformable portion 7110 to its first collapsed configuration. When the entire spinal implant 7100 has been completely collapsed, the spinal implant 7100 can be repositioned between the spinous processes, or removed from its position between the spinous processes and removed from the body in which it was previously inserted. In some embodiments, the first deformable portion 7110 and the second deformable portion 7120 are not completely collapsed, but are instead moved to a configuration between fully expanded and fully collapsed. In this manner the spinal implant 7100 may be repositioned or removed without being completely collapsed.

Figure 13:
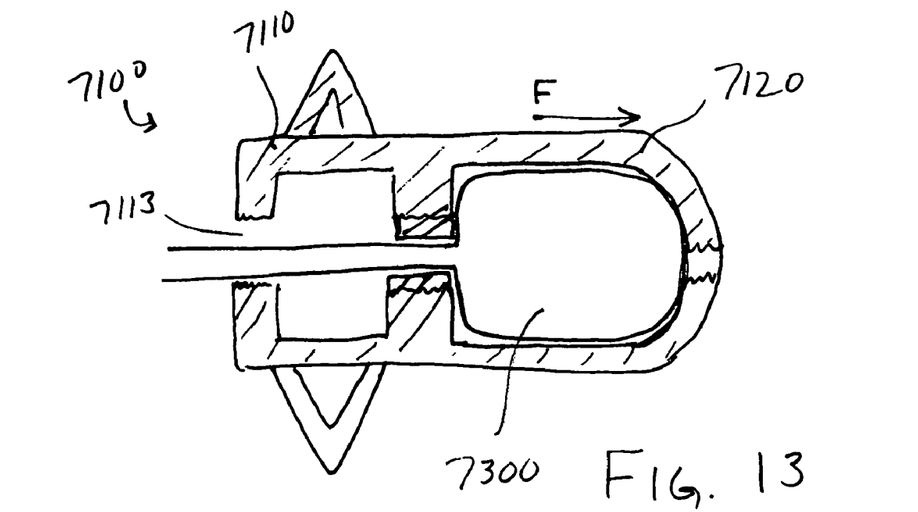
FIG. 13 is a side cross-sectional view of a medical device and an actuator according to an embodiment of the invention with a portion of the medical device moved back to its first configuration.

In some embodiments, the first deformable portion 7110 and the second deformable portion 7120 can be moved between the first and second configuration using a balloon as an actuator. As illustrated in FIG. 13, the second deformable portion 7120 is then moved from the second configuration to the first configuration by imparting a longitudinal force resulting from the inflation of a balloon 7300 with liquid and/or gas. As the balloon 7300 is inflated, it is forced against the central portion 7150 and the second end 7124 of the second deformable portion 7120. The force imparted by the balloon 7300 is generally in the direction indicated by the arrow F. In some embodiments, the balloon 7300 is a low-compliant balloon that is configured to expand to a predefined shape such that a force is imparted primarily in a substantially longitudinal direction indicated by arrow F.

Figure 14:
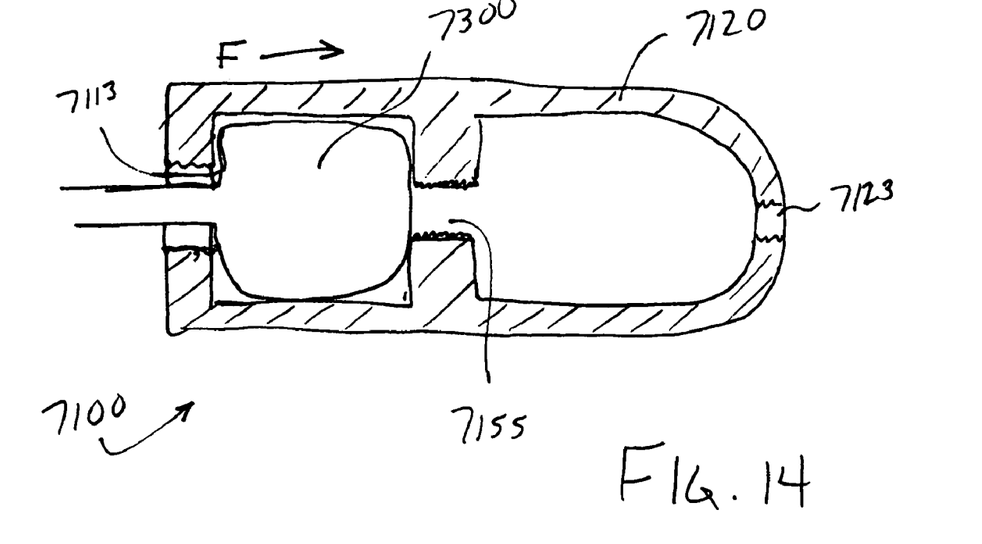
FIG. 14 is a side cross-sectional view of a medical device and an actuator according to an embodiment of the invention with the medical device moved back to its first configuration.

After the second deformable portion 7120 is moved substantially to its collapsed configuration, the balloon 7300 is deflated and moved into the first deformable portion 7110. The balloon 7300 is then inflated as illustrated in FIG. 14 to impart a force in the direction indicated by arrow F. In some embodiments, the same balloon 7300 is used to collapse both the first deformable portion 7110 and the second deformable portion 7120. In other embodiments, a different balloon is used for each portion 7110, 7120. Once the entire implant 7100 is moved to the first configuration, the balloon is deflated and removed. In some embodiments, the balloon 7300 remains in the spinal implant 7100, and the spinal implant 7100 and the balloon 7300 are removed simultaneously.

In some embodiments, the shaft on which the balloon is coupled has external threads (not illustrated) to mate with the first threaded opening 7113, 7113' and/or the second threaded opening 7155, 7155'. In other embodiments, neither the openings nor the shaft on which the balloon is coupled are threaded. In yet other embodiments, the balloon 7300 is inserted through the first portion 7210 of the actuator 7200. Alternatively, the actuator 7200 and the balloon 7300 can be used in conjunction with the spinal implant to expand and/or contract the first deformable portion 7110 and the second deformable portion 7120.

In other embodiments, there are no threaded openings defined in the spinal implant 7100. For example, the spinal implant can have multiple actuator-engaging portions that are not threaded, but are rather contact or bearing surfaces for various types of actuators. For example, an actuator (not illustrated) can be configured to grasp an outer surface of the spinal implant while simultaneously imparting a force against the distal portion of the spinal implant to move the implant to a collapsed configuration.

The spinal implant 7100 can be made from, for example, stainless steel, plastic, polyetheretherketone (PEEK), carbon fiber, ultra-high molecular weight (UHMW) polyethylene, etc. or some combination thereof. For example, the first deformable portion and the second deformable portion can be made from one material and the non-expanding central portion can be made from a different material. The material of such a non-expanding central portion can have a tensile strength similar to or higher than that of bone.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

For example, although the embodiments above are primarily described as being spinal implants configured to be positioned between adjacent spinous processes, in alternative embodiments, the implants are configured to be positioned adjacent any bone, tissue or other bodily structure where it is desirable to maintain spacing while preventing axial or longitudinal movement of the implant.

While the implants described herein were primarily described as not distracting adjacent spinous processes, in alterative embodiments, the implants can be configured to expand to distract adjacent spinous processes.

Although described as being inserted directly between adjacent spinous processes, in alternative embodiments, the implants described above can be delivered through a cannula.

Although the actuator used to move the spinal implant from the expanded configuration to the collapsed configuration is described as a rod assembly or a balloon, in alternative embodiments the actuator can be any device configured to impart a longitudinal force sufficient to move the implant to its collapsed configuration. For example, the actuator can be a piston/cylinder assembly, a ratchet assembly, or the like.

The invention claimed is:

1. A method of implanting an interspinous implant, comprising:
    percutaneously inserting an elongate member into an interspinous space between adjacent spinous processes; the elongate member including a proximal end portion and a distal end portion and a longitudinal axis therebetween; the inserting resulting in the elongate member extending through a sagittal plane defined by the spinous processes with the longitudinal axis disposed transversely to the sagittal plane;
    the proximal end portion comprising a plurality of spaced apart first deformable areas of lowered buckling resistance;
    the distal end portion comprising a plurality of spaced apart second deformable areas of lowered buckling resistance;
    applying a longitudinally compressive load to the elongate member to longitudinally shorten the elongate member so as to move a section of the proximal end portion from a first configuration to a second configuration by buckling and plastically deforming the first deformable areas so that the first deformable areas extend farther away from the longitudinal axis;
    applying a longitudinally compressive load to the elongate member to longitudinally shorten the elongate member so as to move a section of the distal end portion from a first configuration to a second configuration by buckling and plastically deforming the second deformable areas so that the second deformable areas extend farther away from the longitudinal axis;
    wherein the first and second deformable areas thereafter remain in the second configuration absent any force applied to the first and second deformable areas, either external or internal to the elongate member.

2. The method of claim 1, wherein the moving the section of the proximal end portion to its second configuration occurs substantially simultaneously as the moving the section of the distal end portion to its second configuration.

3. The method of claim 1:
    further comprising, thereafter:
        moving the section of the proximal end portion from its second configuration to a third configuration; and
        moving the section of the distal end portion from its second configuration to a third configuration;
    wherein the first configuration of the proximal end portion substantially corresponds to the third configuration of the proximal end portion, and the first configuration of the distal end portion substantially corresponds to the third configuration of the distal end portion.

4. The method of claim 1:
    further comprising, thereafter:
        moving the section of the proximal end portion from its second configuration to a third configuration; and
        moving the section of the distal end portion from its second configuration to a third configuration;
    wherein the first configuration of the proximal end portion differs from the third configuration of the proximal end portion, and the first configuration of the distal end portion differs from the third configuration of the distal end portion.

5. The method of claim 1:
    further comprising, thereafter:
        moving the section of the proximal end portion from its second configuration to a third configuration; and
        moving the section of the distal end portion from its second configuration to a third configuration;
    wherein the moving the section of the proximal end portion to its third configuration and the moving the section of the distal end portion to its third configuration includes imparting an axial load to the elongate member.

6. A method of implanting an interspinous implant, comprising:
    percutaneously inserting an elongate member into an interspinous space between adjacent spinous processes; the elongate member including a proximal end portion and a distal end portion and a longitudinal axis therebetween; the inserting resulting in the elongate member extending through a sagittal plane defined by the spinous processes with the longitudinal axis disposed transversely to the sagittal plane;

the proximal end portion comprising a plurality of spaced apart first deformable areas of lowered buckling resistance;

the distal end portion comprising a plurality of spaced apart second deformable areas of lowered buckling resistance;

applying a longitudinally compressive load to the elongate member to longitudinally shorten the elongate member so as to move a section of the proximal end portion from a first configuration to a second configuration by buckling and plastically deforming the first deformable areas so that the first deformable areas extend farther away from the longitudinal axis;

applying a longitudinally compressive load to the elongate member to longitudinally shorten the elongate member so as to move a section of the distal end portion from a first configuration to a second configuration by buckling and plastically deforming the second deformable areas so that the second deformable areas extend farther away from the longitudinal axis;

wherein the first and second deformable areas thereafter remain in the second configuration absent any force applied to the first and second deformable areas, either external or internal to the elongate member;

further comprising, thereafter:
  moving the section of the proximal end portion from its second configuration to a third configuration; and
  moving the section of the distal end portion from its second configuration to a third configuration;

further comprising coupling an actuator to the elongate member at a first location and a second location before the inserting;

further comprising separating the actuator from the elongate member after the moving the section of the proximal end portion from its first configuration to its second configuration and the moving the section of the distal end portion from its first configuration to its second configuration; and further comprising coupling the actuator to the elongate member before the moving the section of the proximal end portion from its second configuration to its third configuration and the moving the section of the distal end portion from its second configuration to its third configuration.

* * * * *